United States Patent [19]

Picha

[11] Patent Number: 5,207,709
[45] Date of Patent: May 4, 1993

[54] IMPLANT WITH TEXTURED SURFACE

[76] Inventor: George J. Picha, 6554 Beechwood Dr., Independence, Ohio 44131

[21] Appl. No.: 791,917

[22] Filed: Mar. 1, 1993

[51] Int. Cl.⁵ .............................................. A61F 2/02
[52] U.S. Cl. ......................................... 623/11; 623/8; 623/66
[58] Field of Search .................. 623/7, 8, 22, 23, 9, 623/10, 11, 12

[56] References Cited

U.S. PATENT DOCUMENTS

| | | | |
|---|---|---|---|
| 4,385,405 | 5/1983 | Teinturier | 623/23 |
| 4,523,584 | 6/1985 | Yachia et al. | 128/79 A |
| 4,531,244 | 7/1985 | Hamas | 623/8 |
| 4,648,880 | 3/1987 | Brauman . | |
| 4,955,907 | 9/1990 | Ledergerber . | |
| 4,955,909 | 9/1990 | Ersek | 623/7 |
| 4,960,425 | 10/1990 | Yan et al. . | |
| 5,002,572 | 3/1991 | Picha | 623/66 |
| 5,158,571 | 10/1992 | Picha | 623/8 |

Primary Examiner—Randall L. Green
Assistant Examiner—Gina M. Gualtieri
Attorney, Agent, or Firm—Pearne, Gordon, McCoy & Granger

[57] ABSTRACT

An implantable medical device is disclosed. The device has a plurality of fin projections extending from the outer surface of the device, forming a textured exterior surface over at least a portion of the device. Each fin projection has a length substantially greater than its width, the fin projections being arrayed in a basket weave-like, herringbone-like, or other suitable pattern to create a sinuous path for collagen formation around the implanted device. Uses include as a prosthesis, mammary implant, drug mass transport device, and sensor device.

21 Claims, 3 Drawing Sheets

IMPLANT WITH TEXTURED SURFACE

BACKGROUND OF THE INVENTION

This invention relates generally to implantable medical devices and, more particularly, to an improved textured exterior surface thereon having fin projections.

DESCRIPTION OF RELATED ART

When a foreign object is placed in the soft tissue (fascia, muscle, adipose, etc.) of a living body, such as a mammal, animal or human, that body generally attempts to eliminate or isolate the object. Microscopic objects may be engulfed by macrophages and eliminated. Objects which are too large to be engulfed by macrophages tend to be isolated from the body by encapsulation in an envelope of collagen, which is commonly referred to as a fibrous capsule, and which is scar tissue. Most implantable medical devices or surgical implants, including prostheses, tissue expanders, breast or mammary prostheses or implants, mass transport or drug infusion devices, and sensors, are sufficiently large so as to fall into the latter class and, as foreign objects, are encapsulated by the body in a fibrous capsule, frequently in a "classical" tissue response. In a classical tissue response, a relatively thick, dense fibrous capsule or layer of highly oriented collagen forms around the implant after it is implanted. This layer is also referred to as scar tissue. Separated from the implant by the collagen layer are a plurality of fat cells or fascia. Coursing through the fat cells are blood vessels. Some blood vessels will also be found in a collagen layer, but these tend not to be in close proximity to the implant surface. Further, in the classical tissue response, there is a relatively small amount of vascularization.

The fibrous encapsulation of an implantable medical device such as described above can commonly lead to a problem referred to as "capsule contracture." In capsule contracture, the fibrous capsule, over time, contracts and squeezes the implanted medical device. If the device or implant is soft and pliable, such as a human mammary implant, contracture causes the implant to deform and tighten, losing its natural shape and softness, and assuming a minimum volume configuration, i.e., a spherical configuration. Classical tissue response is associated with the problem of capsule contracture. Conversely, non-classical tissue response, as more fully discussed hereinafter, reduces the amount of scar tissue and the thickness of the scar tissue layer, and is believed to be associated with less incidence of capsule contracture and/or less severity of capsule contracture. Smooth-surfaced mammary implants generally lead to a classical tissue response, which, as noted above, is associated with capsule contracture.

In non-classical tissue response, there is a reduced amount of scar tissue and a reduced thickness of the scar tissue layer, more natural vascularity, blood vessels in closer proximity to the implant surface, and, it is believed, less incidence of capsule contracture and/or less severity of capsule contracture.

The formation of a fibrous capsule and a classical tissue response can also adversely impact upon the performance of an implanted mass transport device or sensor. A mass transport device can effect diffusion and/or infusion of a drug into surrounding tissue. The fibrous capsule can form around the device and inhibit diffusion of a therapeutic substance or agent such as a drug away from the mass transport device and/or infusion of such a substance or agent away from such a device and into surrounding tissue, and can inhibit diffusion or transport of a bodily fluid to a sensor for sensing. Diffusion is a passive process responsive to concentration gradients. Infusion is an active process involving the slow introduction of a substance or agent into surrounding tissue. A therapeutic substance such as a drug may be introduced into surrounding tissue by such means as diffusion and infusion. Typically the thicker the capsule is, the more inhibitory it is. When a fibrous capsule forms in connection with a classical tissue response, the vascularity of the body in the area is typically less extensive and is found towards the outer periphery of the fibrous capsule rather than closer to the surface of the implant. This prolongs the lag-phase, or the time that it takes a therapeutic substance such as a drug to get from the mass transport device into the bloodstream or, conversely, the time it takes for a bodily fluid or metabolite to get from the bloodstream to an implanted sensor. This reduces the rate of mass transport and impacts upon the drug delivery profile. In the case of mass transport implants, an increase in vascularity and close proximity of blood vessels to the implant surface is important to provide fast substance exchange between the implant and systemic circulation assuring fast and predictable drug absorption by the body. In the case of sensor implants, increased vascularity and close proximity of vessels to the implant are important to assure fast response times and high sensitivity.

It has been demonstrated that substantial improvement of the vascularization near an implant surface and a reduction in fibrous capsule formation is achieved by presenting the surface morphology of the implant in the form of an array of small, closely spaced projections. These surface projections interfere with the body's ability to form long, somewhat straight, uniform, strong bundles of collagen fibers, referred to as long-range ordering of collagen, which is disadvantageous since such long-range ordering leads to a capsule which is stronger and more likely to contract.

Nonetheless, some long-range ordering of collagen occurs in regular arrays of projections because the pathways between the projections are canyon-like and long. Uninterrupted, straight, canyon-like pathways are present, in which long, somewhat straight collagen bundles can form.

Various textured surfaces have been proposed for implantable devices to solve the problems described above. For example, U.S. Pat. No. 4,960,425 to Yan et al. discloses a surgical prosthesis with a textured surface consisting of a plurality of substantially microscopic peaks and valleys. The depth of the indentations and raised portions is on the order of 7.62 microns to 762 microns, while the width of each individual raised portion or indentation generally ranges in size from 7.62 microns to 2540 microns. Yan et al. further teaches that the projections on the surface of the texturized prosthesis may be generally columnar if a screen with round perforations therein is used as the textured medium, while the projections or indentations may be regular geometric shapes if a screen with a crossed or knitted pattern is used to texturize the surface. However, Yan et al. does not teach specifically the use of fins or fin projections, wherein the fin has a length substantially greater than its width, nor the necessity of utilizing a basket weave-like or herringbone-like arrangement in order to create a sinuous path for collagen deposition around the implant. Yan et al. teaches the preferred texturizing medium to be reticulated foam, which yields projections having irregular shapes.

U.S. Pat. No. 4,955,909 to Ersek et al. teaches a textured silicone implant having randomly placed pillars 20 to 800 microns high. The pillars are of nonuniform length and of non-uniform area (width) and have one or more indentations in the distal end of each pillar. Ersek et al. specifically teaches, at column 5, lines 52 through 62, that projections of uniform length do not reduce the extent of capsule formation.

U.S. Pat. No. 4,955,907 to Ledergerber generally teaches the use of expanded polytetrafluoroethylene (PTFE) as a covering for implantable prosthetic devices. Expanded PTFE is sold under the trade name "GORTEX" and is a fibrous material which has a high degree of ultramicroporosity and is approximately fifty percent air by volume. Ledergerber does not teach the use of pillars or projections as such for reduction in incidence of capsule contracture. In FIGS. 11 and 12 of Ledergerber, nested hexagonal cups are shown. It is taught that the nested hexagonal cups force the scar tissue into concentric, nested rings which do not communicate freely.

U.S. Pat. No. 4,648,880 to Brauman teaches implantable prosthetic devices, such as a mammary implant, with an outer plastic covering which has a rough textured external surface. The outer plastic covering is made of Dacron or Teflon. Brauman does not teach the use of pillars or other projections on the outer surface of the prosthesis.

U.S. Pat. No. 4,531,244 to Hamas teaches a mammary prosthesis with protuberances disposed on the external surface of the prosthesis. However, Hamas does not teach the use of a basket weave-like or herringbone-like arrangement regarding his protuberances, nor a sinuous pathway for collagen formation. Rather, in FIG. 3, he illustrates the surface of the envelope of his prosthesis having a plurality of rigid ridges. The purpose of the ridges is to space the scar tissue that forms upon implantation from the surface of the envelope providing a flow space therebetween into which the envelope may be displaced to permit the prosthesis to change shape. By this technique he attempts to ameliorate the effects of capsule contracture.

U.S. patent application Ser. No. 07/491,225, filed Mar. 9, 1990 entitled "Mammary Implant and Method for Reducing Capsule Contracture", by the applicant herein, teaches a micropillar surface morphology for a mammary implant to reduce the incidence of capsule contracture and to increase non-classical tissue response in connection with an implanted mammary prosthesis. However, the micropillar arrangement does not provide a basket weave-like or herringbone-like fin arrangement, and leaves nonsinuous pathways in which long, straight chains of collagen can form.

The above-referenced U.S. patents are incorporated herein by reference.

None of the foregoing attempts have provided a surface texture morphology which adequately disrupts long-range order in the collagen forming the fibrous capsule. Accordingly, a need exists for an implant textured surface morphology which provides a sinuous path for collagen formation around the implant.

SUMMARY OF THE INVENTION

The present invention provides an implantable medical device which is capable of being implanted in the body tissue of a mammal, such as an animal or human. The implantable device has a supporting structure and a plurality of fin projections extending from the outer surface of the supporting structure. The plurality of fin projections form a textured exterior surface over at least a portion of the implantable device. Each fin projection has a length substantially greater than its width, and the fin projections are arranged in a pattern so as to create a sinuous path for collagen formation around the device. The fin projections can be arrayed in a basket weave-like or herringbone-like pattern or in other suitable array. The device can comprise, for example, a mammary prosthesis, a mass transport device, and a sensor device for sensing a characteristic of a bodily fluid.

The present invention provides implants that significantly alter or eliminate capsule formation by disrupting the long-range ordering of the collagen forming the fibrous capsule. The invention improves the general vascularity about the implant and enhances blood vessel proximity to the implant surface. Improved fixation of the implant is also achieved.

Greater vascularity close to the implant's surface improves the rate at which material, metabolites, drugs, fluids, etc. can be transferred between the body and the implant. This is important for both the infusion of therapeutic substances or agents from a drug infusion device into the body, as well as the measuring of bodily parameters with implanted sensors.

DESCRIPTION OF THE PREFERRED EMBODIMENTS

Figures 1, 2, 3:
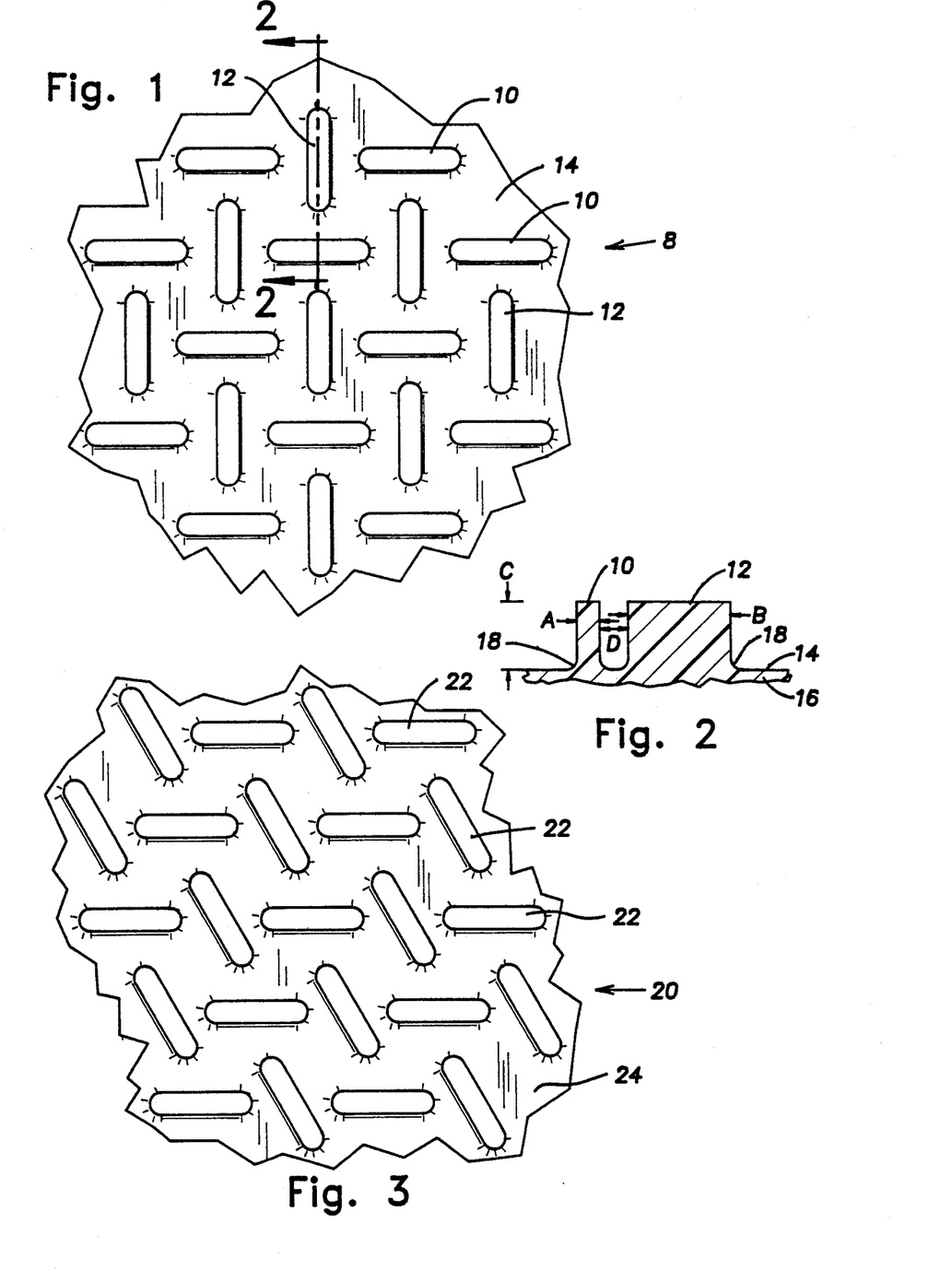
FIG. 1 is a top or plan view of a portion of an implant having a surface morphology in accordance with the present invention.
FIG. 2 is a cross sectional view taken along line 2—2 of FIG. 1.
FIG. 3 is a top or plan view of a portion of an implant having another surface morphology in accordance with the present invention.
Figures 4, 5, 6:
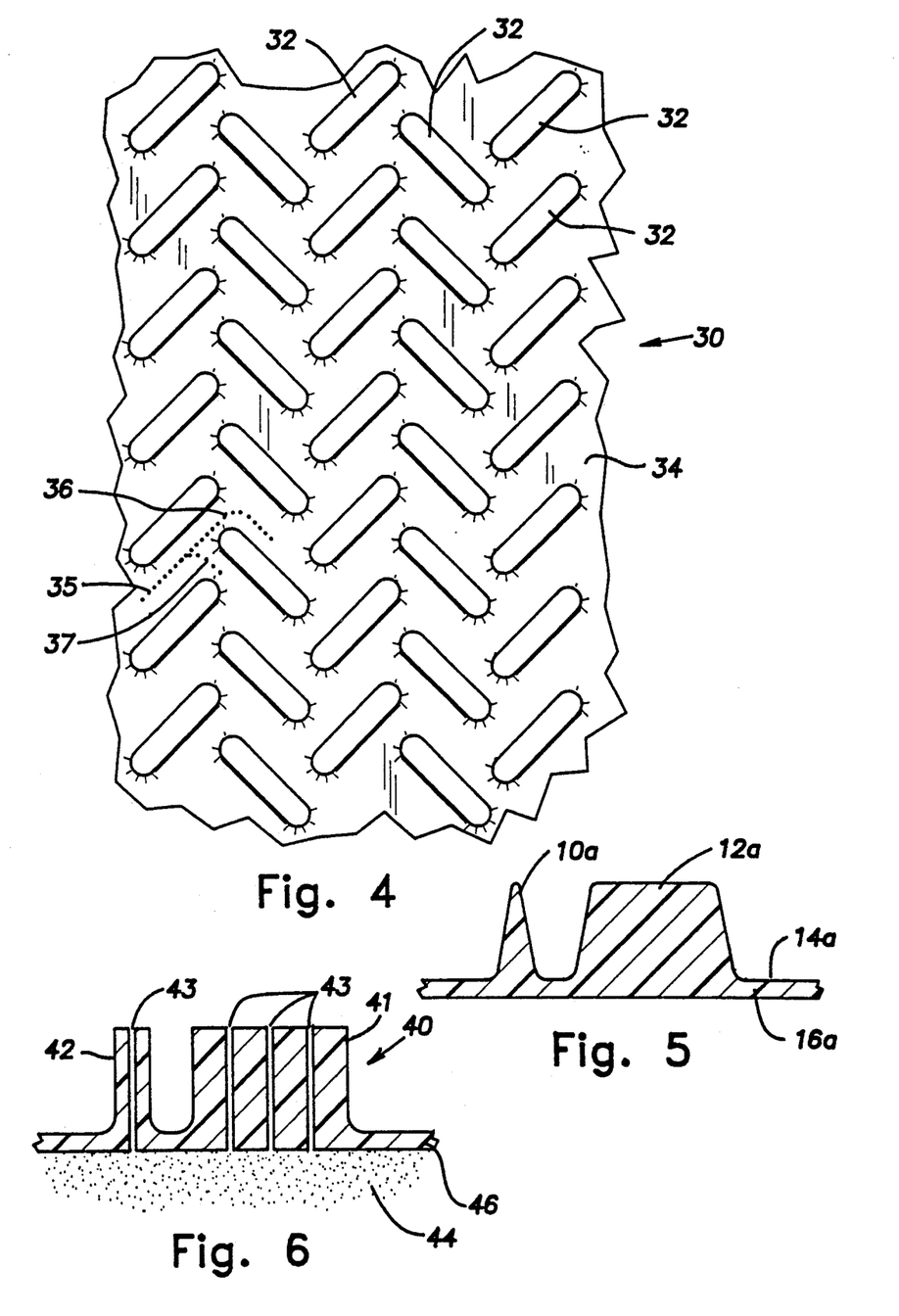
FIG. 4 is a top or plan view of a portion of an implant having another surface morphology in accordance with the present invention.
FIG. 5 is a cross sectional view similar to FIG. 2 showing an additional embodiment of the invention.
FIG. 6 is a cross sectional view similar to FIG. 2 of a portion of a mass transport device illustrating the surface morphology thereof.

FIG. 1 illustrates a portion of an implant 8 having a surface morphology in accordance with the present invention. The implant has a supporting structure which has an outer surface 14. Projecting outwardly from the outer surface are fin projections or fins 10, 12. The fins are shown as being of relatively uniform size and shape and regularly arrayed and are shown as generally the same except for their axial orientation on the outer surface of the implant. The fins need not be of relatively uniform size or shape or regularly arrayed. They may be irregularly or randomly arrayed. As can be seen, the fins are separate and distinct from each other and unconnected. That is, they stand alone and are not joined with each other to form walls, polygonal structures, etc. The fins may extend over less than all of the outer surface area of the supporting structure to form a textured exterior surface; they may also extend over substantially all of it. In FIG. 1, the fins are arrayed in a basket weave-like arrangement or pattern on the outer surface of the implant. Basket weave-like pattern, as used in the claims, means this type of arrangement. This arrangement will disrupt long-range ordering of collagen formation in the fibrous capsule surrounding the implant. The collagen will form next to the surface of the implant between and among the fin projections. The collagen will be forced to form along sinuous, serpentine, wavy, twisting paths, leading to crooked, nonparallel, less strong bundles of collagen fibers. A path is sinuous when it is crooked, constantly changes direction, is twisting, wavy, serpentine, etc. The textured surface of the present invention is characterized by the absence of straight line paths over a significant portion of the textured surface. The paths created in FIGS. 1, 3 and 4 are sinuous. Growth of the fibrous tissue in many different directions or orientations prevents the fibrous tissue from contracting in a concerted manner along straight lines over long distances. In other words, the contractions occur in many directions and tend to neutralize each other. It is also believed that disruption of long-range ordering of collagen formation leads to nonclassical tissue response. Non-classical tissue response is associated with less capsule formation and contracture and improved rate of transfer or mass transport between the body and an implanted mass transport device or sensor device.

The supporting structure and the projections or fins can be made of any suitable implantable or medical grade material, preferably inert, as known in the art, including HP SILASTIC, a high performance silicone elastomer produced by Dow Corning, and other silicone and polymeric elastomers. The material can also be implantable or medical grade ceramics, metals or polymers. The projections or fins can be integrally formed with the supporting structure. For example, the projections or fins may be formed by molding, by lasers, or by the use of milling or ion-beam milling techniques which are known in the art. A plurality of fins on an implant will form a textured exterior surface thereon.

Referring to FIG. 2, a view of the central portion of fin 10 is shown in section. The width of fin 10 is shown at A. The length of fin 12 is shown in section. The length of fin 12 is shown at B. The implant has a supporting structure 16 which has an outer surface or bulk surface 14. Fins 10 and 12 project outwardly from the supporting structure. The height of the fins is shown at C. The sides of the fins are shown as approximately vertical and generally perpendicular to the plane of the supporting structure. The edge proximity spacing is shown at D. Edge proximity spacing is the distance between the end of one fin and the nearest surface of the next or neighboring fin.

The fins are preferably arrayed in a regular pattern on the surface of the implant. However, they may also be arranged in an irregular array, so long as sinuous paths as described above are formed. Each fin has a length substantially greater than its width. The length is about three times the width or more. This enhances the ability to form sinuous paths. The ratio of the length of the fin to the width of the fin can be from about 3:1 up to about 10:1, preferably more than 3:1 and more preferably about 4:1 to about 6:1. Preferably, each fin is about 100 to about 1000 microns wide, more preferably about 200 to about 500 microns wide. Preferably, the edge proximity spacing is about the same as the width of the fin.

Preferably the height of the fins is substantially uniform and is between about 200 and about 2500 microns, more preferably about 1000 to about 2000 microns high. The fin dimensions and spacing are mean values and variations within customary manufacturing methods will occur. The sides need not necessarily be vertical with respect to the supporting structure, nor flat. They may be tapered. If surfaces are tapered, etc., then generally average measurements or distances will be used for width, length, height, spacing, etc.

Referring to FIG. 2, the fins preferably have a thickened portion or fillet 18 at the base. The thickened portion 18 provides a smooth joint between the fin and the supporting structure 16 which tends to inhibit the development of stress risers. The thickened portion 18 also increases the strength of the attachment between the fin 10, 12 and the supporting structure 16. The concave shape of the thickened portion distributes the stress forces, inhibiting cracking or fracturing.

The top of the fin 10, 12 is shown as flat. It can also be convex or concave or combinations thereof. The ends of the fin are shown as rounded but can also be flat or otherwise shaped.

Referring to FIG. 3, another embodiment of a surface morphology in accordance with the present invention is illustrated. A portion of an implant 20 is shown. The outer surface 24 of the supporting structure is shown. Projecting outwardly from the outer surface of the supporting structure are fin projections or fins 22, which are arrayed in an approximately herringbone-like arrangement or pattern to create a sinuous path for collagen deposition or formation around the implanted device.

Referring to FIG. 4, another embodiment of a surface morphology in accordance with the present invention is illustrated. A portion of an implant 30 is shown. The outer surface 34 of the supporting structure is shown. Projecting outwardly from the outer surface of the supporting structure are fin projections or fins 32, which are arrayed in a herringbone-like arrangement or pattern to create a sinuous path for collagen formation. With particular reference to the herringbone-like pattern or arrangement of FIG. 4, it is noted that the pathways in which collagen can form are frequently bifurcated or split or forked. Pathway 35 thus splits into pathways 36 and 37, forming multiple subpathways. The arrangement of fins generally requires or encourages the collagen bundles of fibers to split or fork or bifurcate at frequent and/or regular intervals.

Referring to FIG. 5, another embodiment of the invention is illustrated. FIG. 5 illustrates a view similar to that of FIG. 2, showing a different shape for the fin. The width of fin 10a is shown in cross section; the length of fin 12a is shown in cross section. In this configuration the width and length can be the average width and average length, respectively. The fins 10a, 12a project outwardly from the outer surface 14a of the supporting structure 16a. The sides of the fins are sloped to make it easier to demold the implant device during the molding process. The sloped sides also may permit the fins to better penetrate tissue in the body.

Referring to FIG. 6, a portion of an implantable mass transport device 40 is shown. A mass transport device may look, for example, like a large pill and may be used for dispensing medication such as insulin. The mass transport device has a surface morphology with fin projections as described and illustrated above. A mass transport device holds a therapeutic substance such as a drug that is slowly diffused or leaked or leached or infused or otherwise introduced into the body tissue surrounding the device after the device has been implanted. Two fins, 41 and 42, similar to the fins illustrated in FIG. 2, are shown. Orifices or infusion ports 43 have been provided in the fins to allow a therapeutic substance 44 such as a drug to diffuse or infuse or travel through the orifices into the bodily tissue adjacent to the implanted device. The mass transport device has a supporting structure 46 which is preferably approximately 0.040 inches thick. The fins are formed integrally with the supporting structure and are preferably solid silicone as described above, except for the orifices. The orifices can be holes, typically 50 to 350 microns in diameter, preferably about 200 microns. Alternatively the orifice can be a slit.

Figure 7:
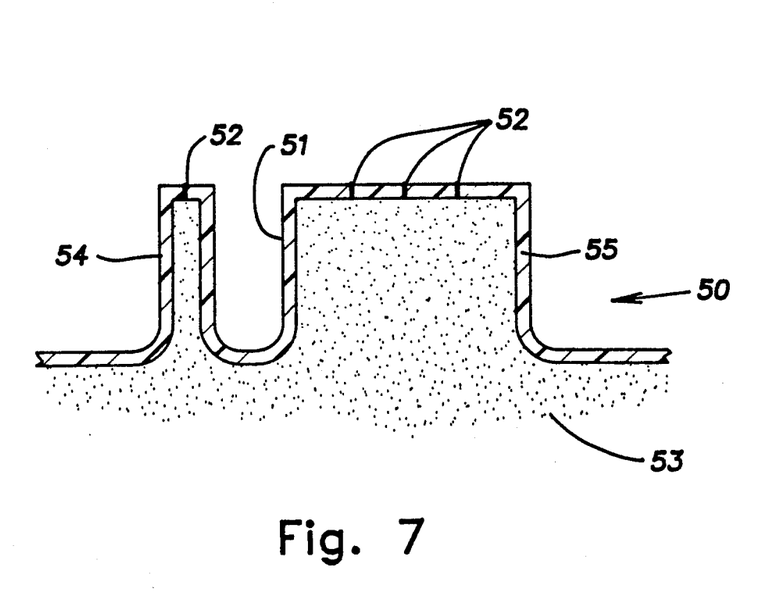
FIG. 7 is a cross sectional view similar to FIG. 6 illustrating the surface morphology of a mass transport device according to another embodiment of the invention.

Referring to FIG. 7, a portion of an implantable mass transport device 50 is shown. The mass transport device has a surface morphology with fin projections as described and illustrated above and with regard to FIG. 6, except that the fins are not solid; they have cavities or voids in their interior as shown in FIG. 7. These cavities or voids are preferably interconnected between fins. Fins 51, 54 are shown, similar in relationship to fins 12, 10 of FIG. 2 and fins 41, 42 of FIG. 6. The mass transport device has a self-supporting membrane 55 which defines the exterior surface and shape of the fins and the mass transport device. The fins may have orifices or infusion or diffusion ports 52, which are typically holes or slits. If the orifices are holes, they are typically 30 to 350 microns in diameter, preferably about 200 microns. The diffusion ports are usually located on top of the fin, but may be at other locations. Diffusion ports permit a therapeutic substance 53 such as a drug to diffuse or be infused from the mass transport device 50 into the body in which the device is implanted. The therapeutic substance is held within the cavities or voids defined by the self-supporting membrane 55 and in the interior of the device.

The self-supporting membrane 55 is typically made of polycarbonate, cellulose acetate, cellulose nitrate or silicone and is typically 5 to 100 microns thick, preferably about 10 microns. If the material is non-permeable, diffusion ports are necessary. If the material is permeable, or semipermeable, such as some forms of cellulose acetate, holes or slits may not be necessary but may be utilized. Silicone is less rigid than the other materials mentioned but some structure can be provided by the presence of the therapeutic substance 53. With regard to permeable or semipermeable self-supporting membranes, porosity is generally maintained at less than approximately 0.1 microns to exclude cells and certain proteins.

The self-supporting membrane 55 can also be made of semipermeable material, such as a block copolymer of styrene and hydroxyethylmethacrylate, or cellulose acetate, typically 5 to 20 microns thick; preferably approximately 5 microns thick. Membrane-covered fins such as illustrated in FIG. 7 are particularly useful for drug diffusion purposes as well.

Figure 8:
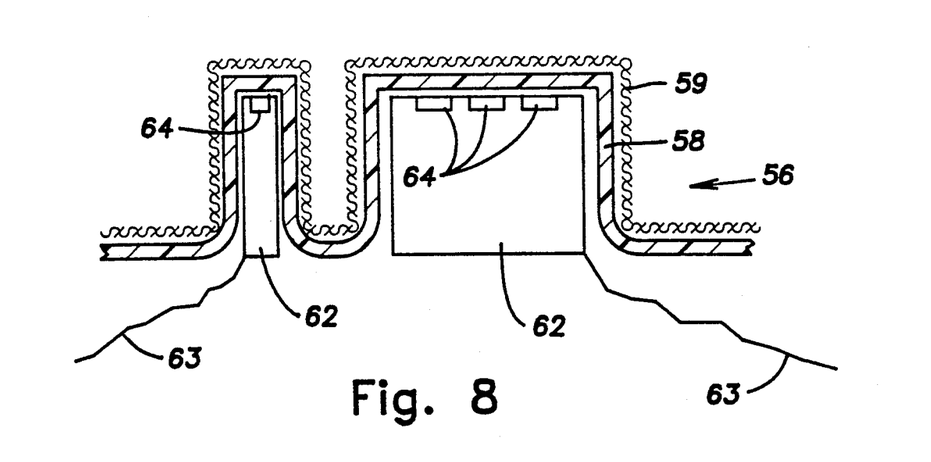
FIG. 8 is a cross sectional view similar to FIG. 2 of a portion of a sensor device according to the present invention.

Referring to FIG. 8, a portion of an implantable sensor device 56 for sensing and/or measuring a characteristic of a bodily fluid is shown. Such a device may look, for example, much like a pill or disk. The implantable sensor device 56 has a surface morphology with fins as illustrated and described above; see, for example, FIGS. 2 and 7. Within one or more fins a sensor 62 may be placed or imbedded. The sensor 62, to measure a bodily parameter or characteristic or metabolite of a bodily fluid (e.g. oxygen, blood sugar, pH, etc.), is covered by a self-supporting structure or membrane 58. The self-supporting membrane 58 may be covered by a non-self-supporting membrane 59.

The sensor 62 may have electrodes or sensing elements 64 for purposes of electrical or electronic sensing. For example, the sensor may be provided with electrodes, counter-electrodes, and reference electrodes. A wire 63 connects the sensor 62 to means for powering, controlling, and providing a readout for the sensor. Such means may be internal or external to the implantable sensor device 56.

The self-supporting membrane may be made of epoxy, polycarbonate, polystyrene or other suitable material. It is typically approximately 5 to 50 microns thick, preferably about 5 microns thick. It may be porous, open latticework, or provided with slits or holes. These means permit bodily fluid to interact with the sensing means by, among other things, admitting the bodily fluid, which comprises molecules, to be sensed. Orifice includes a slit and a hole. The pores may be more than 0.1 microns in diameter when the non-self-supporting membrane has sufficiently small openings to act as an exclusion membrane. The self-supporting membrane may also be semipermeable, with a thickness of typically 5 to 250 microns.

The non-self-supporting membrane 59 can be made of a compliant material. It can be porous and is typically a semipermeable membrane made of material such as cellulose acetate, having a thickness typically 5 to 50 microns, preferably about 5 microns. The pore size of the non-self-supporting membrane is typically less than 0.1 microns to exclude cells and certain proteins so as to not foul the sensor.

Optionally a second or third layer of open microfoam can be added to induce blood vessel proximity and neovascularization. A typical open microfoam is polyvinylalcohol foam with a pore size of 10 microns to 50 microns. Optionally, orifices such as indicated at 43 in FIG. 6 can be added to sensor device 56 by enlarging the fin, reducing the size of the sensor, etc. to make room for the orifice, with additional orifices in the membranes as appropriate. A further modification is a combined mass transport and sensor device including fins as shown in FIGS. 6 and/or 7, together with fins as shown in FIG. 8.

In operation, the sensor device 56 is implanted in the soft tissue where the bodily fluid having the characteristic to be sensed is conveniently available. The fluid is admitted through the non-self-supporting membrane 59 and/or through interacting means such as slits, orifices, holes or pores in the self-supporting membrane 58, where it contacts or interacts with the sensor 62. Alternatively, no separate technique for admitting fluid is necessary; one and/or both membranes may be compatible with remote sensing so that the membranes operate as the interacting means. The fluid is sensed and/or measured by the electrodes or sensing elements 64 and/or the sensor 62. Also, in many applications it is preferable to coat the non-self-supporting membrane directly onto the sensor, avoiding the need for the self-supporting membrane. In such a case the thickness is typically 0.5 microns to 25 microns, preferably 5 microns or less.

The cavities or voids in the fins of FIG. 8 which are filled with the sensor 62 can also be filled with therapeutic substances such as drugs as in FIG. 7 and the device can be used as a mass transport device as described with respect to FIG. 7.

The presence of the arrangement of fins or fin projections on the surface of the implantable medical device, be it a prosthesis, breast implant, tissue expander, mass transport device, or sensor device, etc., has at least three effects. First, the fin arrangement disrupts the long-range ordering of the collagen forming the fibrous capsule. The fins are oriented so as to form sinuous pathways along which the collagen will form, thus diminishing the straight line strength of the collagen. Long, straight bundles of collagen fibers are stronger and less compliant and form a stronger fibrous capsule than collagen fibers which are shorter or which are oriented in multiple directions, leading to less overall strength.

Second, the fins provide mechanical anchorage; that is, they penetrate into the surrounding tissue, such as fatty tissue, and hold the implant in place. The tendency for sheer movement, which is a sliding movement along the interface between the implant and the surrounding tissue, is reduced due to a mechanical load transfer from the tissue to the implant. It is more difficult for fins to penetrate fascia or muscle tissue. In contrast, fatty tissue is far more compliant and more easily penetrated by fins or projections.

Third, the surface fins can disrupt the polymerization of the collagen forming the fibrous capsule. The interface between the implant and the surrounding tissue is constantly irritated or through the mechanical sheer of the microstructure with the surrounding tissue, reduces the amount of polymerized collagen.

It is believed that these factors contribute substantially to a non-classical response of a body to an implant with projections of the present invention. It has been shown that an implant with fin projections according to the present invention has led to a non-classical tissue response; see the Example which follows. The non-classical response is preferred, since it results in less scar tissue and is believed to result in a reduced incidence of capsule contracture. Further, the fibrous capsule is reduced in size or eliminated; blood vessel proximity to the implant surface is enhanced and the degree of vascularity is also increased. This leads to improved rates of mass transfer or mass transport between the body and the implanted mass transport device or sensor device.

EXAMPLE

A study was conducted which utilized implants consisting of disks 1 cm in diameter and 1 mm thick cast from two-part silicone rubber (Dow Corning MDX4-4210). Projections, when present, were integrally molded on both sides of the disk.

Male Sprague-Dawley rats, 250-300 gm, were utilized. Four dorsal incisions, bilateral anterior and posterior, were made. The subcutaneous plane was bluntly dissected for some distance away from the incision site and the implants inserted. One face of the disk faced outward toward the dermis; the other faced inward toward the fascia.

In this aspect of the experiment about sixty disks were implanted, and two surface morphologies (designated "A" and "B") and one control (designated "O") were tested. The control was a flat, smooth-surfaced disk with no surface texture. Projection A had a surface morphology as illustrated in FIGS. 1 and 2 wherein the width of the fin was 250 microns, the length of the fin was 1500 microns, the height of the fin was 1000 microns, and the edge proximity spacing was 200 microns. Projection B had a surface morphology as illustrated in FIGS. 1 and 2 wherein the width of the fin was 400 microns, the length of the fin was 2400 microns, the height of the fin was 2000 microns, and the edge proximity spacing was 400 microns.

An attempt was made to distribute the different surface morphologies, including the flat disk with no surface texture as a control, equally between the four implant sites. After one month, the implants and pelts were harvested and analyzed. Each face of the disk was rated as to whether or not the animal's response to that face was nonclassical, as described above. Also, the capsule thickness adjacent to the bulk surface of the implant was measured, and the blood vessel proximity was measured in microns to the nearest surface; this could either be the bulk surface or the pillar surface.

Implant surfaces facing the dermis were not as revealing as those facing the fascia, since little adipose or fat tissue exists in the dermis. In Table 1 the capsule thickness is given for disks facing the fascia.

The fascia on the posterior of the animal contained more fatty tissue than the fascia on the anterior of the animal. The posterior implants were accordingly considered more pertinent. In Tables 2 and 3 are given the percent nonclassical response for disks facing the fascia and dermis, respectively. In Tables 4 and 5 the blood vessel proximity to the nearest surface is given for disks facing the fascia and dermis, respectively, measured in microns; this surface could be either the bulk surface or the pillar surface.

In the Tables, the control is indicated as Projection O. Anterior ("ANT") means the disk was implanted anteriorly in the region of the scapula; posterior ("POS") means the disk was implanted posteriorly in the lateral abdominal area. All measurements are in microns.

TABLE 1

Capsule Thickness for Disks Facing The Fascia

| PROJECTION | SITE | CAPSULE THICKNESS |
|---|---|---|
| O | ANT | 89.9 |
| O | POS | 138.0 |
| A | ANT | 96.5 |
| A | POS | 34.9 |
| B | ANT | 73.1 |
| B | POS | 41.0 |

TABLE 2

Percent Nonclassical Response, Disks Facing Fascia

| PROJECTION | SITE | PERCENTAGE |
|---|---|---|
| O | ANT | 0 |
| O | POS | 0 |
| A | ANT | 0 |
| A | POS | 20 |
| B | ANT | 60 |
| B | POS | 75 |

TABLE 3

Percent Nonclassical Response, Disks Facing Dermis

| PROJECTION | SITE | PERCENTAGE |
|---|---|---|
| O | ANT | 0 |
| O | POS | 0 |

TABLE 3-continued

Percent Nonclassical Response, Disks Facing Dermis

| PROJECTION | SITE | PERCENTAGE |
| --- | --- | --- |
| A | ANT | 0 |
| A | POS | 10 |
| B | ANT | 30 |
| B | POS | 0 |

TABLE 4

Blood Vessel Proximity For Disks Facing The Fascia

| PROJECTION | SITE | BLOOD VESSEL PROXIMITY |
| --- | --- | --- |
| O | ANT | 31.5 |
| O | POS | 95.1 |
| A | ANT | 30.0 |
| A | POS | 16.5 |
| B | ANT | 25.5 |
| B | POS | 26.5 |

TABLE 5

Blood Vessel Proximity For Disks Facing The Dermis

| PROJECTION | SITE | BLOOD VESSEL PROXIMITY |
| --- | --- | --- |
| O | ANT | 67.5 |
| O | POS | 100.8 |
| A | ANT | 34.2 |
| A | POS | 33.4 |
| B | ANT | 36.4 |
| B | POS | 38.0 |

From these Tables it can be seen that both projections A and B (the disks with fin projections on the surface) did better than the smooth control (Projection O), and of the two fin morphologies, B was the better of the two. In Table 1, the posterior sites are the more pertinent. The capsule thickness for the control was 138.0 microns, while the thickness was 34.9 and 41.0 microns, respectively, for the A and B projections, a dramatic improvement. As discussed previously, a thinner capsule is much better and much preferred. In Tables 2 and 3, it can be seen that the percent nonclassical response was improved with regard to the fin surfaces over the smooth control, and was particularly and dramatically improved with regard to the B fin projection surface. Tables 4 and 5 show that blood vessel proximity improved significantly when one went from the smooth control to the textured surfaces with fin projections. Blood vessel proximity is important for faster drug absorption by the body and faster response time with regard to sensors, as described above. These results demonstrate that significantly improved results are obtained when the surface of the implant is textured with fin projections in accordance with the present invention, particularly the fin projections of morphology B.

The foregoing experiments are considered an appropriate model for human biologic response. Medical devices having a textured exterior surface of fin projections in accordance with the present invention are implanted in accordance with known techniques used for the implantation of medical devices.

It should be evident that this disclosure is by way of example and that various changes may be made by adding, modifying, or eliminating details without departing from the fair scope of the teaching contained in this disclosure. The invention is therefore not limited to particular details of this disclosure except to the extent that the following claims are necessarily so limited.

What is claimed is:

1. An implantable medical device for implanting into soft tissue of a mammal, said implantable device comprising a supporting structure, said supporting structure having an outer surface for interface with the soft tissue and a plurality of fin projections extending from said outer surface, said plurality of fin projections forming a textured exterior surface over at least a portion of said implantable device, each fin projection having a length substantially greater than its width, said fin projections being arranged in a pattern so as to create a sinuous path for collagen formation around the device and to substantially eliminate straight-line paths for collagen formation around the device.

2. The implantable device of claim 1, wherein said fin projections are arrayed in a basket weave pattern.

3. The implantable device of claim 1, wherein said fin projections are arrayed in a herringbone pattern.

4. The implantable device of claim 1, wherein said fin projections are arranged in an irregular array.

5. The implantable device of claim 1, wherein the device is a mammary prosthesis.

6. The device of claim 1, wherein the ratio of the length of the fin projection to the width of the fin projection is between about 3:1 and about 10:1.

7. The device of claim 6, wherein the ratio is more than 3:1.

8. The device of claim 6, wherein the ratio is between about 4:1 and about 6:1.

9. The device of claim 1, wherein the height of the fin projections is substantially uniform and is between about 200 and about 2500 microns.

10. The device of claim 2, wherein each fin projection is about 2000 microns high, about 400 microns wide, and about 2400 microns long.

11. An implantable medical device for implanting into soft tissue of a mammal, said implantable device comprising a supporting structure, said supporting structure having an outer surface for interface with the soft tissue and a plurality of fin projections extending from said outer surface, said plurality of fin projections forming a textured exterior surface over at least a portion of said implantable device, each fin projection having a length substantially greater than its width, said fin projections being arranged in a pattern so as to create a sinuous path for collagen formation around the device, the device being capable of containing a therapeutic substance, said device having means whereby said therapeutic substance may be introduced in a controlled manner into the soft tissue surrounding the device.

12. The implantable device of claim 11, wherein said device has means whereby said therapeutic substance may be introduced via said fin projections into the soft tissue surrounding the device.

13. The device of claim 11, wherein said means comprise slits.

14. The device of claim 11, wherein said means comprise holes.

15. The device of claim 11, wherein said means comprise a semipermeable membrane.

16. The device of claim 11, wherein said means comprise a membrane having a porosity less than 0.1 microns.

17. An implantable medical device for implanting into soft tissue of a mammal, said implantable device comprising a supporting structure, said supporting structure having an outer surface for interface with the soft tissue and a plurality of fin projections extending from said outer surface, said plurality of fin projections forming a textured exterior surface over at least a portion of said implantable device, each fin projection having a length substantially greater than its width, said fin projections being arranged in a pattern so as to create a senuous path for collagen formation around the device, the device including means for sensing a characteristic of a bodily fluid, said device further having interacting means for enabling bodily fluid to interact with said sensing means.

18. The device of claim 17, wherein said sensing means is contained within one of said fin projections.

19. The device of claim 17, wherein said interacting means comprises a membrane having orifices.

20. The device of claim 17, wherein said interacting means comprises a semipermeable membrane.

21. The device of claim 17, wherein said interacting means comprises a membrane having a porosity less than 0.1 microns.

* * * * *

UNITED STATES PATENT AND TRADEMARK OFFICE
CERTIFICATE OF CORRECTION

PATENT NO. : 5,207,709

DATED : May 4, 1993

INVENTOR(S) : George J. Picha

It is certified that error appears in the above-identified patent and that said Letters Patent is hereby corrected as shown below:

On the title page, the item [21] the Filing Date, delete "March 1, 1993" and insert --November 13, 1991--.

Column 13, Claim 17, line 6, delete "senuous" and insert --sinuous--.

Signed and Sealed this

Eleventh Day of January, 1994

*Attest:*

BRUCE LEHMAN

*Attesting Officer*     *Commissioner of Patents and Trademarks*